United States Patent [19]
Arnold et al.

[11] 4,021,458
[45] May 3, 1977

[54] PROCESS FOR THE PREPARATION OF 3-HEMISULFATE-17α-HYDROXY STEROIDS

[75] Inventors: Hanfried Arnold; Jean-Claude Hilscher; Reinhold Wieske, all of Berlin, Germany

[73] Assignee: Schering Aktiengesellschaft, Berlin & Bergkamen, Germany

[22] Filed: Apr. 15, 1975

[21] Appl. No.: 568,379

[30] Foreign Application Priority Data

Apr. 18, 1974  Germany .......................... 2419207

[52] U.S. Cl. ............................................. 260/397.5
[51] Int. Cl.² ............................................. C07J 1/00
[58] Field of Search ...................... 260/397.4, 397.5

[56] References Cited

UNITED STATES PATENTS

| | | | |
|---|---|---|---|
| 2,666,066 | 1/1954 | Hasbrouck | 260/397.4 |
| 2,917,522 | 12/1959 | Price | 260/397.4 |
| 3,836,527 | 9/1974 | Irmscher et al. | 260/397.4 |

FOREIGN PATENTS OR APPLICATIONS

| | | | |
|---|---|---|---|
| 810,917 | 3/1959 | United Kingdom | 260/397.4 |
| 829,618 | 3/1960 | United Kingdom | 260/397.4 |

*Primary Examiner*—Elbert L. Roberts
*Attorney, Agent, or Firm*—Millen & White

[57] ABSTRACT

3-Hemisulfate sodium salts of 17α-hydroxy steroids of the formula

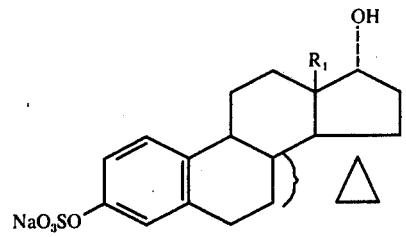

wherein $R_1$ is H, $CH_3$ or $C_2H_5$ and $\Delta$ is one or more additional double bonds optionally present in the B and/or C rings are produced by treating a 17-mono ester of a carboxylic acid of up to 15 carbon atoms of the corresponding 3,17α-dihydroxy steroid with the reaction product of pyridine or like amine and sulfur trioxide or reactive functional derivative thereof and, without isolation thereof, saponifying the resultant reaction product with alkali, preferably a sodium alcoholate or hydroxide in a lower alcohol.

10 Claims, No Drawings

PROCESS FOR THE PREPARATION OF 3-HEMISULFATE-17α-HYDROXY STEROIDS

BACKGROUND OF THE INVENTION

This invention relates to a process for the production of 3-hemisulfate sodium salts of 17α-hydroxy steroids of the general Formula I

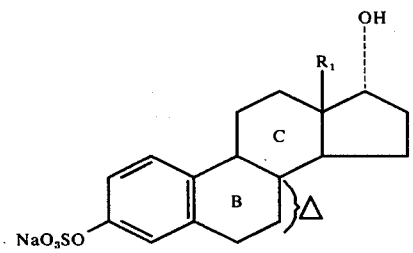

wherein $R_1$ is hydrogen, methyl or ethyl and Δ represents one or more additional double bonds optionally present in either or both of rings B and C.

These compounds are valuable pharmaceuticals and can be utilized, due to their estrogenic activity, inter alia, for mitigating the physical and mental complaints connected with the climacteric.

A combination of compounds of Formula I wherein $R_1$ is methyl and wherein, firstly, there is no additional double bond (sodium 17α-estradiol-3-hemisulfate), secondly, a $\Delta^7$-double bond is present (sodium 17α-dihydroequilin-3-hemisulfate), and, thirdly, the $\Delta^{6,8}$-double bonds are present (sodium 17α-dihydroequilenin-3-hemisulfate), are components of medicinal preparations obtained as a mixture ("natural conjugated estrogens") together with the corresponding 17-ketones from the urine of pregnant mares.

The ratio of the individual estrogens in the pregnant mare urine, however, is dependent on the stage of the pregnancy. The resulting fluctuations must be compensated for by the addition of varying amounts of the individual components (Canadian Pat. Nos. 691,988 and 922,627) in order to produce a uniform product.

A synthetic process is known for the manufacture of sodium estradiol-3-hemisulfate. This process is disclosed in Canadian Pat. Nos. 482,630 and 482,631. (For the novel nomenclature employed, see, for example, "Steroids," Fieser and Fieser, publishers Chemie/Weinheim, pp. 511–512.)

This synthesis involves three separate stages. In the first stage, 17α-estradiol-17-acetate is reacted with chlorosulfonic acid in pyridine to produce 17α-estradiol-3-hemisulfate-17-acetate pyridinium salt. In the second stage, this pyridinium salt is converted, with sodium hydroxide, to the sodium 17α-estradiol-17-acetate-3-hemisulfate. In the third stage, the latter compound is saponified in the presence of aqueous alkali hydroxide by heating to 100° C. to the sodium salt of 17α-estradiol-3-hemisulfate. This process is relatively complicated, due to the isolation twice of intermediate products by precipitation with ether and the very expensive extraction of the final product in acetone. Also, the thus-attained overall yields are only around 35% of theory.

It is an object of the present invention to provide a simple synthetic method for the production of sodium hemisulfates of aromatic A-ring 3,17α-dihydroxy estrogens. Other objects will be apparent to those skilled in the art.

SUMMARY OF THE INVENTION

According to the process of a 17-acyloxy mono ester of a 3,17-dihydroxy steroid corresponding to the desired product, i.e., a 3-hydroxy-17α-acyloxy steroid of the general Formula II

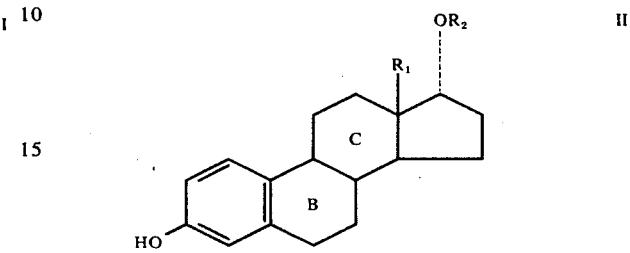

wherein $R_1$ is hydrogen, methyl or ethyl, $R_2$ is the acyl radical of an organic carboxylic acid of up to 15 carbon atoms, or a corresponding steriod having one or more additional double bonds in the B and C rings, is treated with sulfur trioxide or an agent transferring sulfur trioxide, i.e., a reactive functional derivative of sulfur trioxide, in an organic amine; and without isolation thereof, converting the reaction product into the corresponding sodium hemisulfate 3-mono ester by treatment with an alkaline sodium compound, preferably sodium alcoholate or sodium hydroxide in a lower alcohol, with simultaneous saponification.

DETAILED DISCUSSION

Examples of double bonds which optionally can be present in rings B and C of the steroid molecule are, for example, the $\Delta^6$-, $\Delta^7$-, $\Delta^{9(11)}$-, and $\Delta^{6,8}$-double bonds.

Preferred starting compounds of general Formula II are those wherein
 a. $R_1$ is $CH_3$;
 b. Δ is 0, 1 or 2 double bonds, which are preferably a $\Delta^7$ or $\Delta^{6,8}$ double bonds;
 c. Ac is alkanoyl, preferably of 1–6 carbon atoms, especially those of (a) and (b).

It will be apparent to those skilled in the art that because the 17-acyloxy group is saponified in the second step of the process of this invention, although the preferred acyloxy groups are those whose acyl radical is that of an alkanoic acid, more preferably of 1–6 carbon atoms and most preferably acetic acid, functional equivalents thereof in the process of this invention are those starting compounds wherein the acyl radical is that of other organic acids, e.g., a carboxylic acid containing up to 15 carbon atoms, especially lower (1–6) and intermediate (7–12) aliphatic carboxylic, preferably an alkanoic acid, which can be unsaturated, branched, polybasic, or substituted in the usual manner, for example by hydroxy or halogen atoms; a cycloaliphatic, aromatic or a mixed aromatic-aliphatic (alkaryl and aralkyl) acid, which can likewise be substituted in the usual manner. Thus, in addition to the acyl radicals of the preferred acids, e.g., acetic acid, propionic acid, butyric, isobutyric, α-methylbutyric, valeric, isovaleric, α-methylvaleric, 2-ethylbutyric, 3-ethylbutyric and diethylacetic and caproic acid, equivalent are the acyl radicals of acids containing 1–18, preferably 2–12 carbon atoms, including an aliphatic acid containing 1–18, preferably 1–6 carbon atoms, e.g., triethylacetic, enanthic, octanoic, undecylic, oleic and palmitic acid; a cyclic acid, preferably a cycloaliphatic acid, containing, e.g., 5–18 carbon atoms, e.g., cyclopropylideneacetic, cyclobutylcarboxylic, cyclopentylcarboxylic, cyclopentylacetic, cyclohexyl, cyclohexylacetic, cyclopentylpropionic and β-cyclohexylpropionic acid; a carboxyxlic aryl or alkaryl acid, e.g., containing 6–18 carbon atoms, and 1–5, preferably 1 or 2 rings, e.g., benzoic, 2-, 3-, or 4-methylbenzoic, 2,3-, 2,4-, 2,5-, 2,6-, 3,4-, and 3,5-dimethylbenzoic, ethylbenzoic, 2,3,6-trimethylbenzoic, and 3-methyl-α-naphthoic acid; an aralkyl acid, e.g., containing 7–18 carbon atoms, e.g., phenylacetic and β-phenylpropionic, a polybasic acid, e.g., malonic, succinic, including those containing 2–18 carbon atoms and 1–5 hydroxy groups, e.g., glycolic, lactic, citric, tartaric, d-maleic, d-glyceric, and salicylic acid; the corresponding acids containing one, two or more of simple substituents, e.g., halo, alkoxy, acyloxy, etc., in the molecule, e.g., chloroacetic, fluoroacetic, dichloroacetic, trichloroacetic, trifluoroacetic, 2,3,4-trimethoxybenzoic, phenoxyacetic, α-naphthoxyacetic acid, etc.

The sulfur trioxide or reactive functional derivative thereof, i.e., an agent capable of transferring sulfur trioxide, such as, for example, chlorosulfonic acid or amidosulfonic acid, is suitable introduced into the amine, such as, for example, pyridine and like heterocyclic aromatic amines, e.g., picoline, quinoline and collidine; tertiary aromatic amines, e.g., dimethylaniline; and tertiary aliphatic amines, e.g., trimethylamine, triethylamine; tertiary carboxylic amines, e.g., N-methylpiperidine, or like amine capable of forming a complex with sulfur trioxide but otherwise unaltered thereby, by the gradual introduction thereof at temperatures of below 0° C.

The 3-hydroxy-17α-acyloxy steroid is then preferably added to the thus-formed complex. However, it is also possible to add the reaction product of the amine and the sulfur trioxide or transfer agent therefor, to a solution of the steroid. The usual reaction time is several hours, e.g., 3 to 24 hours or longer at room temperature and correspondingly longer and shorter times at lower and higher temperatures. Generally, a temperature below about 0° or above 60° C is not employed because of excessively long reaction times and undesirable side reactions, respectively. The sulfur trioxide transfer agent is preferably employed in a molar equivalent excess. Preferably, 1.1–5 molar equivalents are employed.

After termination of the reaction, any excess sulfur trioxide transfer agent is destroyed with a small amount of water, and then without isolation thereof, the reaction product is saponified with an alkaline sodium salt, preferably an alcoholic solution of a sodium alcoholate, sodium methylate or sodium hydroxide, for example, by introduction thereof into the reaction solution. The mixture is then preferably allowed to stand again for several hours at room temperature to ensure complete reaction of the alkali with the intermediate reaction product, i.e., form the sodium hemisulfate salt at the 3-position and saponify the ester at the 17-position.

The sodium alcoholate or hydroxide is suitable added diluted in alcohol in a small molar excess in such a quantity that the pH of the reaction mixture ranges preferably between 9 and 11. Usually, 0.1–2 moles excess alcoholate or hydroxide is required to reach a pH of 9–11.

After cessation of the reaction, the mixture is neutralized with a dilute acid, such as, for example, methanolic hydrochloric acid, separated from the insoluble matter, the solvents are distilled off, and the mixture is further worked up and purified in a conventional manner, e.g., by reprecipitation and purification by chromatography and the sodium hemisulfate mono ester isolated.

Those compounds having one or more double bonds in the B and C rings can be selectively hydrogenated in a conventional manner to the corresponding B and C ring-saturated estrogens.

It was surprising that the axial 17α-ester group can be split off under the very gentle reaction conditions employed in the process of this invention, for example, treatment with a dilute alcoholic sodium alcoholate or sodium hydroxide solution at room temperature. Ordinarily, the axial substituent, the 17α-ester group can be saponified, as is known, only under great difficulties with alkali or acids. "Analyt. Chem." (1963) 35 1243.

The process of this invention has the advantage that the desired final products, e.g., the components of the conjugates of the natural estrogens, are obtained in a single-stage process in high yields.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

0.8 ml. of sulfur trioxide is added dropwise to 20 ml. of pyridine at −20° C. At room temperature, a solution of 2.0 g. of 17α-acetoxy-1,3,5(10)-estratrien-3-ol [prepared from the 3,17α-diacetate analogously to Miescher, Helv.Chim.Acta 20, 263 (1937)] in 6 ml. of pyridine is added to this solution, and the mixture is allowed to stand for 7 hours at room temperature under a stream of nitrogen gas. The excess complex is destroyed with 0.8 ml. of water, diluted with 45 ml. of methanol, adjusted to pH 10.5 with 34.4 ml. of 1N sodium methylate solution, and allowed to stand for 7 hours at room temperature. The mixture is neutralized with 1N methanolic hydrochloric acid; the thus-precipitated insoluble inorganic salts are filtered off, the methanol is distilled off at 55° C. under vacuum, the residue is taken up in 30 ml. of pyridine, separated by filtration from insoluble inorganic salts, and the filtrate is precipitated into ether. Yield: 2.0 g. (84% of theory) of sodium 17α-estradiol-3-hemisulfate. The crude product is further purified by treatment with carbon and reprecipitation from methanol/ether; m.p. 157° C. (decomposition). $[\alpha]_D = +39.8°$ (methanol). 99% strength according to thin-layer chromatography.

EXAMPLE 2

1.6 g. of sulfur trioxide is added dropwise at −20° C. to 20 ml. of pyridine. At room temperature, a solution of 4.0 g. of 17α-acetoxy-1,3,5(10),7-estratetraen-3-ol [prepared from the 3,17α-diacetate analogously to Miescher, Helv.Chim. Acta 20, 263 (1937), m.p. 130°–134° C., $[\alpha]_D = +134.9°$] in 20 ml. of pyridine is added to this solution, and the mixture is allowed to stand at room temperature for 7 hours. The complex is destroyed with 1.6 ml. of water, diluted with 90 ml. of methanol, and set to pH 10.5 with 1N sodium methylate solution. After allowing the mixture to stand at room temperature for 7 hours, it is worked up as indicated in Example 1, thus obtaining 4.1 g. of a 94% product which is purified by reprecipitation from methanol/ether and treatment with carbon. Sodium 17α-hydroxy-1,3,5(10),7-estratetraen-3-ol-3-hemisulfate is thus produced as a white, water-soluble powder; m.p. 156° C. $[\alpha]_D = +153°$ (methanol). Uniform in accordance with thin-layer chromatography.

EXAMPLE 3

2.0 g. of 17α-acetoxy-1,3,5(10),6,8-estrapentaen-3-ol [prepared from the 3,17α-diacetate analogously to Miescher, Helv.Chim.Acta 20, 263 (1937), m.p. 187°–188° C. $[\alpha]_D = -25.8°$] is reacted, as described in Example 1, with the sulfur trioxide/pyridine complex. The complex is destroyed with 0.8 ml. of water, and the suspension is set to pH 10.5 after adding 45 ml. of methanol, with the use of 1N sodium methylate solution. After 7 hours, the saponification is finished, and the mixture is worked up as set forth in Example 1, thus obtaining 1.9 g. of sodium 17α-hydroxy-1,3,5(10),6,8-estrapentaen-3-ol-hemisulfate; m.p. 165° C. $[\alpha]_D = -4.4°$ (methanol). Uniform in accordance with thin-layer chromatography.

EXAMPLE 4

A solution of 2 g. of 17α-acetoxy-1,3,5(10)-estratrien-3-ol [prepared from the 3,17α-diacetate analogously to Miescher, Helv.Chim.Acta 20, 263 (1937)] in 10 ml. of pyridine is added gradually to a solution of 0.56 ml. of chlorosulfonic acid in 20 ml. of pyridine; the mixture is allowed to stand for 16 hours at room temperature under a stream of nitrogen gas. After adding 0.4 ml. of water, the mixture is diluted with 45 ml. of methanol; 30 ml. of a 1N methanolic sodium hydroxide solution is added thereto, and the mixture is allowed to stand at room temperature for 7 hours. The mixture is thereafter worked up as disclosed in Example 1, yielding 1.7 g. of sodium 17α-estradiol-3-hemisulfate; m.p. 153° C. (decomposition). $[\alpha]_D = +38.7°$ (methanol). Uniform according to thin-layer chromatography.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the production of a 3-hemisulfate sodium salt of a 17α-hydroxy steroid of the formula

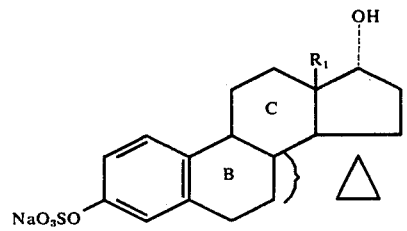

wherein $R_1$ is hydrogen, methyl, or ethyl and Δ is 0 to 3 double bonds in the B and C rings, which comprises treating a corresponding 3-hydroxy-17α-acyloxy steroid of the formula

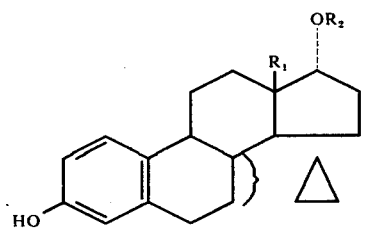

wherein $R_1$ and Δ have the values given above and $R_2$ is the acyl radical of an organic carboxylic acid of up to 15 carbon atoms, or a corresponding steroid having 1–3 double bonds in the B and C rings, with sulfur trioxide in an amine or with a reactive functional derivative of sulfur trioxide capable of transferring sulfur trioxide, in an amine at about 0°–60° C.; and saponifying the reaction product without isolation thereof with an alkaline sodium compound.

2. A process according to claim 1, wherein in the first step the starting steroid is reacted with the reaction product of sulfur trioxide and pyridine at about 0°–60° C.

3. A process according to claim 1, wherein in the first step the starting steriod is reacted with the reaction product of chlorosulfonic acid and pyridine.

4. A process according to claim 1, wherein the alkaline sodium compound is a sodium alcoholate or sodium hydroxide.

5. A process according to claim 1, wherein the alkaline sodium compound is a sodium methylate in methanol.

6. A process according to claim 1, wherein $R_1$ is $CH_3$.

7. A process according to claim 6, wherein the starting steroid is 17α-acetoxy-1,3,5(10)-estratrien-3-ol, 17α-acetoxy-1,3,5(10),7-estratetraen-3-ol, or 17α-acetoxy-1,3,5(10),6,8-estrapentaen-3-ol.

8. A process according to claim 1, wherein the starting steroid is reacted with sulfur trioxide in pyridine, or chlorosulfonic acid in pyridine at about room temperature.

9. A process according to claim 1, wherein the product of the first reaction is reacted at a pH of 9–11 with one or both of sodium hydroxide and sodium methylate.

10. A process according to claim 7, wherein the starting steroid is reacted with sulfur trioxide in pyridine, or with chlorosulfonic acid in pyridine and wherein the product of the first reaction is reacted at a pH of 9–11 with one or both of sodium hydroxide and sodium methylate.

* * * * *

UNITED STATES PATENT AND TRADEMARK OFFICE
CERTIFICATE OF CORRECTION

PATENT NO. : 4,021,458
DATED : May 3, 1977
INVENTOR(S) : HANFRIED ARNOLD ET AL.

It is certified that error appears in the above-identified patent and that said Letters Patent are hereby corrected as shown below:

Claim 2 should read:

-- 2. A process according to Claim 1, wherein in the first step the starting steroid is reacted with the reaction product of sulfur trioxide and pyridine. ---.

Signed and Sealed this fifth Day of July 1977

[SEAL]

Attest:

RUTH C. MASON
Attesting Officer

C. MARSHALL DANN
Commissioner of Patents and Trademarks